US006245888B1

(12) United States Patent
Staddon

(10) Patent No.: US 6,245,888 B1
(45) Date of Patent: Jun. 12, 2001

(54) PROTEINS INVOLVED IN THE REGULATION OF CELL—CELL ADHESION AND USES THEREOF

(75) Inventor: James Martin Staddon, London (GB)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 08/874,197

(22) Filed: May 19, 1997

Related U.S. Application Data

(63) Continuation-in-part of application No. PCT/GB95/02686, filed on Nov. 16, 1995.

(30) Foreign Application Priority Data

Nov. 18, 1994 (GB) .................................................. 9423372

(51) Int. Cl.[7] .............................. C07K 1/00; C07K 14/00; C07K 17/00; A61K 38/00
(52) U.S. Cl. .............................................. 530/350; 514/12
(58) Field of Search .............................. 530/350; 514/12; 435/7.1, 69.1, 320.1, 325; 536/23.1

(56) References Cited

FOREIGN PATENT DOCUMENTS

WO 95/13820    5/1995  (WO) .

OTHER PUBLICATIONS

Harper's Review of Biochemistry 20th edition p. 17, 1985.*
Chen et al Molecular and Cellular Biology vol. 14 p. 4501, Jul. 1994.*
Gura, Science vol. 278 p. 1041, Nov. 1997.*
Osband et al Immunology Today vol. 11 p. 193, 1990.*
Johnson et al, Cancer Treatement Reviews vol. 2 p. 1, 1975.*
Hyafil, F. et al., "A Cell Surface Glycoprotein Involved in the Compaction of Embryonal Carcinoma Cells and Cleavage Stage Embryos," *Cell* 21:927–934 (1980).
Aghib, D.F. and P.D. McCrea, "The E–cadherin Complex Contains the src Substrate p120," *Exp. Cell Res.* 218:359–369 (1995).
Behrens, J. et al., "Dissecting Tumor Cell Invasion: Epithelial Cells Acquire Invasive Properties after the Loss of Uvomorulin–mediated Cell–Cell Adhesion," *J. Cell Biol.* 108:2435–2447 (1989).
Birchmeier, W. and J. Behrens, "Cadherin expression in carcinomas: role in the formation of cell junctions and the prevention of invasiveness," *Biochim. et Biophys. Acta* 1198:11–26 (May 1994).
Boller, K. et al., "Cell–Adhesion Molecule Uvomorulin is Localized in the Intermediate Junctions of Adult Intestinal Epithelial Cells," *J. Cell Biol.* 100:327–332 (1985).
Daniel, J.M. and A.B. Reynolds, "The Tyrosine Kinase Substrate p120$^{cas}$ Binds Directly to E–Cadherin but Not to the Adenomatous Polyposis Coli Protein or α–Catenin," *Mol. Cell. Biol.* 15(9):4819–4824 (1995).

Downing, J.R. and A.B. Reynolds, "PDGF, CSF–1, and EGF induce tyrosine phosphorylation of p120, a pp60$^{src}$ transformation–associated substrate," *Oncogene* 6:607–613 (1991).
Franke, W.W. et al., "Molecular cloning and amino acid sequence of human plakoglobin, the common junctional plaque protein," *Proc. Natl. Acad. Sci. USA* 86:4027–4031 (1989).
Frixen, U.H. et al., "E–Cadherin–mediated Cell–Cell Adhesion Prevents Invasiveness of Human Carcinoma Cells," *J. Cell Biol.* 113(1):173–185 (1991).
Gumbiner, B. and K. Simons, "A Functional Assay for Proteins Involved in Establishing an Epithelial Occluding Barrier: Identification of a Uvomorulin–Like Polypeptide," *J. Cell Biol.* 102:457–468 (1986).
Gumbiner, B. et al., "The Role of the Cell Adhesion Molecule Uvomorulin in the Formation and Maintenance of the Epithelial Junctional Complex," *J. Cell Biol.* 107:1575–1587 (1988).
Hatzfeld, M. et al., "Band 6 protein, a major constituent of desmosomes from stratified epithelia, is a novel member of the armadillo multigene family," *J. Cell Sci.* 107:2259–2270 (Aug. 1994).
Hedrick, L. et al., "Cell adhesion molecules as tumour suppressors," *Trends in Cell Biol.* 3:36–39 (Feb. 1993).
Herrenknecht, K. et al., "The uvomorulin–anchorage protein α catenin is a vinculin homologue," *Proc. Natl. Acad. Sci. USA* 88:9156–9160 (1991).
Hirano, S. et al., "Calcium–dependent Cell–Cell Adhesion Molecules (Cadherins): Subclass Specificities and Possible Involvement of Actin Bundles," *J. Cell Biol.* 105:2501–2510 (1987).
Hirano, S. et al., "Identification of a Neural α–Catenin as a Key Regulator of Cadherin Function and Multicellular Organization," *Cell* 70:293–301 (1992).
Jou, T–S. et al., "Genetic and biochemical dissection of protein linkages in the cadherin–catenin complex," *Proc. Natl. Acad. Sci. USA* 92:5067–5071 (1995).
Kanner, S.B. et al., "Monoclonal antibodies to individual tyrosine–phosphorylated protein substrates of oncogene–encoded tyrosine kinases," *Proc. Natl. Acad. Sci. USA* 87:3328–3332 (1990).

(List continued on next page.)

*Primary Examiner*—Sheela Huff
*Assistant Examiner*—Alana M. Harris
(74) *Attorney, Agent, or Firm*—Sterne, Kessler, Goldstein & Fox P.L.L.C.

(57) ABSTRACT

A protein, p100, is disclosed having a molecular weight of about 100 kDa, being associated in vivo with catenin-cadherin complex of epithelial or endothelial cells, and having cross-reactivity with an antibody to the p120 protein involved in cell-cell adhesion. Also disclosed is a method to treat a cancer or developmental disorder characterized by compromised cell-cell adhesion.

2 Claims, 10 Drawing Sheets

OTHER PUBLICATIONS

Kanner, S.B. et al., "Tyrosine Phosphorylation of a 120–Kilodalton pp60$^{src}$ Substrate upon Epidermal Growth Factor and Platelet–Derived Growth Factor Receptor Stimulation and in Polyomavirus Middle–T–Antigen–Transformed Cells," *Mol. Cell. Biol.* 11(2):713–720 (1991).

Kikuchi, A. et al., "Molecular cloning of the human cDNA for a stimulatory GDP/GTP exchange protein for c–Ki–ras p21 and smg p21," *Oncogene* 7:289–293 (1992).

Kintner, C., "Regulation of Embryonic Cell Adhesion by the Cadherin Cytoplasmic Domain," *Cell* 69:225–236 (1992).

Kinzler, K.W. et al., "Identification of FAP Locus Genes from Chromosome 5q21," *Science* 253:661–665 (1991).

Knudsen, K.A. and M.J. Wheelock, "Plakoglobin, or an 83–kD Homologue Distinct from β–catenin, Interacts with E–cadherin and N–cadherin," *J. Cell Biol.* 118(3):671–679 (1992).

Linder, M.E. and J.G. Burr, "Nonmyristoylated p60$^{v-src}$ fails to phosphorylate proteins of 115–120 kDa in chicken embryo fibroblasts," *Proc. Natl. Acad. Sci. USA* 85:2608–2612 (1988).

Matsuzaki, F. et al., "cDNAs of Cell Adhesion Molecules of Different Specificity Induce Changes in Cell Shape and Border Formation in Cultured S180 Cells," *J. Cell Biol.* 110:1239–1252 (1990).

McCrea, P.D. and B.M. Gumbiner, "Purification of a 92–kDa Cytoplasmic Protein Tightly Associated with the Cell–Cell Adhesion Molecule E–cadherin (Uvomorulin)," *J. Biol. Chem.* 266(7):4514–4520 (1991).

McCrea, P.D. et al., "A Homolog of the armadillo Protein in Drosophila (Plakoglobin) Associated with E–Cadherin," *Science* 254:1359–1361 (1991).

McManus, M.J. et al., "Tissue– and Transformation–Specific Phosphotyrosyl Proteins in v–erbB–Transformed Cells," *J. Virology* 69(6):3631–3638 (1995).

Musil, L.S. et al., "Differential Phosphorylation of the Gap Junction Protein Connexin43 in Junctional Communication–competent and –deficient Cell Lines," *J. Cell Biol.* 11:2077–2088 (1990).

Nagafuchi, A. and M. Takeichi, "Cell binding function of E–cadherin is regulated by the cytoplasmic domain," *EMBO J.* 7(12):3679–3684 (1988).

Nagafuchi, A. et al., "The 102 kd Cadherin–Associated Protein: Similarity to Vinculin and Posttranscriptional Regulation of Expression," *Cell* 65:849–857 (1991).

Nelson, W.J., "Regulation of Cell Surface Polarity from Bacteria to Mammals," *Science* 258:948–955 (1992).

Ozawa, M. et al., "The cytoplasmic domain of the cell adhesion molecule uvomorulin associates with three independent proteins structurally related in different species," *EMBO J.* 8(6):1711–1717 (1989).

Ozawa, M. et al., "Uvomorulin–catenin complex formation is regulated by a specific domain in the cytoplasmic region of the cell adhesion molecule," *Proc. Natl. Acad. Sci. USA* 87:4246–4250 (1990).

Peifer, M. and E. Wieschaus, "The Segment Polarity Gene armadillo Encodes a Functionally Modular Protein That Is the Drosophila Homolog of Human Plakoglobin," *Cell* 63:1167–1178 (1990).

Peifer, M. et al., "The Vertebrate Adhesive Junction Proteins β–catenin and Plakoglobin and the Drosophila Segment Polarity Gene armadillo Form a Multigene Family with Similar Properties," *J. Cell Biol.* 118(3):681–691 (1992).

Peifer, M. et al., "A Repeating Amino Acid Motif Shared by Proteins with Diverse Cellular Roles," *Cell* 76:789–791 (Dec. 1994).

Piepenhagen, P.A. and W.J. Nelson, "Defining E–cadherin–associated protein complexes in epithelial cells: plakoglobin, β– and γ–catenin are distinct components," *J. Cell Sci.* 104:751–762 (Mar. 1993).

Reynolds, A.B. et al., "Transformation–Specific Tyrosine Phosphorylation of a Novel Cellular Protein in Chicken Cells Expressing Oncogenic Variants of the Avian Cellular src gene," *Mol. Cell. Biol.* 9(2):629–638 (1989).

Reynolds, A.B. et al., "p120, a novel substrate of protein tyrosine kinase receptors and of p60$^{v-src}$, is related to cadherin–binding factors β–catenin, plakoglobin and armadillo," *Oncogene* 7:2439–2445 (1992).

Reynolds, A.B. et al., "Identification of a New Catenin: The Tyrosine Kinase Substrate p120 (cas) Associates with E–Cadherin Complexes," *Mol. Cell. Biol.* 5:448a, abstract No. 2609 (Oct. 1994).

Reynolds, A.B. et al., "Identification of a New Catenin: the Tyrosine Kinase Substrate p120$^{cas}$ Associates with E–Cadherin Complexes," *Mol. Cell. Biol.* 14(12):8333–8342 (Dec. 1994).

Riggleman, B. et al., "Molecular analysis of the armadillo locus: uniformly distributed transcripts and a protein with novel internal repeats are associated with a Drosophila segment polarity gene," *Genes & Dev.* 3:96–113 (1989).

Rubin, L.L. et al., "A Cell Culture Model of the Blood–Brain Barrier," *J. Cell Biol.* 115(6):1725–1753 (1991).

Rubin, L.L., "Endothelial cells: adhesion and tight junctions," *Curr. Opin. Cell Biol.* 4:830–833 (1992).

Rubinfeld, B. et al., "Association of the APC Gene Product with β–Catenin," *Science* 262:1731–1734 (Dec. 1993).

Shibamoto, S. et al., "Association of p120, a Tyrosine Kinase Substrate, with E–Cadherin/Catenin Complexes," *J. Cell Biol.* 128(5):949–957 (1995).

Shimoyama, Y. et al., "Cadherin Cell–Adhesion Molecules in Human Epithelial Tissues and Carcinomas," *Cancer Res.* 49:2128–2133 (1989).

Shimoyama, Y. et al., "Cadherin Dysfunction in a Human Cancer Cell Line: Possible Involvement of Loss of α–Catenin Expression in Reduced Cell–Cell Adhesiveness," *Cancer Res.* 52:5770–5774 (1992).

Staddon, J.M. et al., "Evidence that tyrosine phosphorylation may increase tight junction permeability," *J. Cell Sci.* 108:609–619 (1995).

Staddon, J.M. et al., "p120, a p120–Related Protein (p100), and the Cadherin/Catenin Complex," *J. Cell Biol.* 130(2):369–381 (1995).

Su, L–K. et al., "Association of the APC Tumor Suppressor Protein with Catenins," *Science* 262:1734–1737 (Dec. 1993).

Takeichi, M., "Cadherin Cell Adhesion Receptors as Morphogenetic Regulator," *Science* 251:1451–1455 (1991).

Tsukita, S. et al., "Specific Proto–Oncogenic Tyrosine Kinases of src Family Are Enriched in Cell–to–Cell Adherens Junctions Where the Level of Tyrosine Phosphorylation Is Elevated," *J. Cell Biol.* 113(4):867–879 (1991).

Tsukita, S. et al., "Submembranous Junctional Plaque Proteins Include Potential Tumor Suppressor Molecules," *J. Cell Biol.* 123(5):1049–1053 (Dec. 1993).

Vleminckx, K. et al., "Genetic Manipulation of E–Cadherin Expression by Epithelial Tumor Cells Reveals an Invasion Suppressor Role," *Cell* 66:107–119 (1991).

Yano, R. et al., "Cloning and Characterization of SRP1, a Suppressor of Temperature–Sensitive RNA Polymerase I Mutations, in *Saccharomyces cerevisiae*," *Mol. Cell. Biol.* *12*(*12*):5640–5651 (1992).

Yano, R. et al., "Yeast Srp1p has homology to armadillo/plakoglobin/β–catenin and participates in apparently multiple nuclear functions including the maintenance of the nucleolar structure," *Proc. Natl. Acad. Sci. USA* *91*:6880–6884 (Jul. 1994).

* cited by examiner

| HUMAN p100 | MOUSE p120 | |
|---|---|---|
| SEQUENCER RESULTS | PUBLISHED SEQUENCE | RESIDUES |
| NISFGRDQDNK | NISFGRDQDNK | 434–444 |
| HAIPNLV | HARPNLV | 744–751 |
| XVLINK | LVLINK | 799–804 |
| XPIEDPANDTVDFPX | KPTEDPANDTVDFPX | 629–642 |
| XPSGALRNLAVDARX (Tentative) | AASGALRNLAVDARK | 723–738 |

FIG. 9

PROTEINS INVOLVED IN THE REGULATION OF CELL— CELL ADHESION AND USES THEREOF

CROSS REFERENCE TO RELATED APPLICATION

The present application is a continuation-in-part of PCT application PCT/GB95/02686 filed Nov. 16, 1995.

BACKGROUND OF THE INVENTION

Field of the Invention

The present invention relates to certain proteins which may be involved in regulating physiological changes (e.g. changes in cell-cell adhesion) and to uses thereof.

Cell adhesion is important for a wide variety of regulatory and developmental processes. The cadherins comprise a family of transmembrane, cell surface glycoproteins that mediate $Ca^{2+}$-dependent cell-cell adhesion in a homotypic manner (Takeichi, 1991). In cells with well developed intercellular junctions, the cadherins are localized to the adherens junction (Boller et al., 1985) but appear to influence other intercellular junctions such as gap junctions (Matsuzaki et al., 1990; Musil et al., 1990) and tight junctions (Gumbiner and Simons, 1986; Gumbiner et al., 1988). The adherens junction also plays a crucial role in the development and maintenance of cell polarity (see Nelson, 1992) and its dysfunction has been strongly implicated in the invasiveness and carcinogenesis of tumour cells (see e.g. Behrens et al., 1989; Frixen et al., 1991; Vleminckx et al., 1991; Shimoyama et al., 1992; and Hedrick et al., 1993; Tsukita et al., 1993; Birchmeier and Behrens, 1994).

The conserved cytoplasmic domain of cadherins is known to associate with three proteins, termed α-β-and γ-catenin (Pzawa et al., 1989), which serve to link cadherins to the actin-based cortical cytoskeleton (Hirano et al., 1987). The association of cadherins with catenins is essential for intercellular $Ca^{2+}$-dependent adhesiveness (Nagafuchi and Takeichi, 1988; Ozawa et al., 1990; Kintner, 1992). α-catenin is homologous to vinculin (Herrenknecht et al., 1991; Nagafuchi et al., 1991), making it a good candidate for interaction with the actin-based cytoskeleton (see Ozawa et al., 1990; Hirano et al., 1992). β-catenin is homologous to the Drosophilia segment polarity gene *armadillo*, suggesting a role in developmental signalling in vertebrates (McCrea et al., 1991). γ-catenin is probably identical to plakoglobin (Knudsen and Wheelock, 1992; but see Piepenhagen and Nelson, 1993), which again is homologous to *armadillo* (see Franke et al., 1989; Peifer and Wieschaus, 1990). Indeed, β-catenin and plakoglobin appear to form a multigene family (Peifer et al., 1992)

A repeating 42 amino acid motif that was originally identified in *armadillo* (Riggleman et al., 1989) has also been found in several other proteins, including β-catenin and plakoglobin, with a variety of functions (Peifer et al, 1994). These include the APC gene product, a tumor suppressor protein (Kinzler et al., 1991), p120, a $pp60^{STC}$ substrate (Reynolds et al., 1992), smgGDS, an exchange factor for ras-related G proteins (Kikuchi et al., 1992), a suppressor of RNA polymerase I mutations in yeast (Yano et al., 1992; 1994) and band 6 protein, a major desmosomal constituent (Hatzfeld et al., 1994). The function of the repeats in these arm proteins is unknown. Interestingly, the APC gene product associates with β-catenin (Rubinfeld et al., 1993; Su et al., 1993), supporting an important role for catenins in intracellular processes that regulate cell growth. Furthermore, this illustrates that cadherins are not exclusive cellular partners of catenins, raising the possibility of other interactions among catenins, cadherins and arm proteins, important in a variety of biological processes.

p120 was initially identified as one of several substrates of the tyrosine kinase $pp60^{src}$ (Reynolds et al., 1989; Kanner et al., 1990). It is membrane-associated and can be myristoylated, but does not appear to be glycosylated (Kanner et al., 1991). Mutational analysis suggested that tyrosine phosphorylation of p120 is necessary for of $pp60^{STC}$-mediated cellular transformation (Linder and Burr, 1998/ Reynolds et al., 1989). Tyrosine phosphorylation of p120 was also observed in response to epidermal growth factor, platelet-derived growth factor, colony-stimulating factor 1 and in polyoma virus middle T antigen-transformed cells (Dowing and Reynolds, 1991; Kanner et al., 1991), but the exact role of p120 in cellular physiology and pathology was not clear.

SUMMARY OF THE INVENTION

According to the present invention, there is provided a protein having a molecular weight of about 100 kDa which is associated in vivo with the cadherin/catenin complex of epithelial or endothelial cells (e.g. by binding). This protein is referred to herein as "p100". p100 is immunologically related to p120 by virtue of cross-reactivity of antibody to p120 with p100.

DETAILED DESCRIPTION OF THE PREFERRED EMBODIMENTS

Partial amino acid sequence data of human p100 is given in FIG. 9 (SEQ ID NOS.: 1 through 5) where it is compared with sequence data already available for mouse p120 (SEQ ID NOS.: 1 and 6 through 9). The present invention covers the specific protein of molecular weight of about 100 kDa described in the present examples and other proteins having substantial amino-acid homology therewith (excluding p120, and optionally also excluding proteins having greater amino acid homology with p120 than with p100). Human p100 is particularly preferred.

The term "substantial amino acid homology" is used herein to cover proteins having at least 50%, preferably more than 90% or more than 95% amino acid homology with another protein. The present invention also covers fragments of these proteins or of p100 itself. Preferably these fragments are at least twenty amino acids long, more preferably they are at least fifty or at least one hundred amino acids long. These proteins or fragments may be partially or totally tyrosine phosphorylated. They may be provided in glycosylated or non-glycosylated form. Desirably they are provided in substantially pure form. One definition of "substantially pure form" is a form which is substantially free of other proteins.

The present invention also includes nucleic acid sequences (preferably DNA sequences) coding for the above mentioned proteins or fragments. These sequences may be in isolated form. They may be incorporated as part of a recombinant nucleic acid molecule e.g. as part of a vector. The vector may be incorporated into a host cell and used for expression of p100.

Nucleic acid sequences complementary to the aforesaid sequences may be useful in antisense studies to alter the expression of gene products. Such sequences are therefore also within the scope of the present invention.

In view of the data provided herein, it is believed that the protein p100 may be involved in the regulation of cell tight junction permeability. Phosphorylation of one or more tyrosine residues of p100 may be involved in increasing tight junctions permeability and dephosphorylation of one or more tyrosine residues may be involved in decreasing tight junction permeability. The above comments also apply in respect of p120, which the present inventors have shown to be immunologically closely related to p100.

p100 and p120 are therefore useful for studying cell-cell adhesion generally and tight junction permeability in particular. They may therefore be used, for example, to investigate the effect of tyrosine kinase and/or of tyrosine phosphatase on tight junction permeability. Variants of these proteins may be prepared in order to investigate which regions of p100 or p120 are important in regulating tight junction permeability.

Our data indicate that p120 and p100 associate with the cadherin/catenin complex. Furthermore, since p120 and p100 are substrates for tyrosine kinases, it follows that p120 and p100 proteins per se and the phosphorylation of these proteins may influence cellular functions directly, and indirectly, regulated by cadherins and catenins. Such an influence could be mediated by the physical association between p120, p100 and the cadherin/catenin complex, in which case modulation could be achieved by enhancing or blocking the expression of p120 and p100. Disruption of the association could also be achieved, for example, by small molecule mimetics of the site of binding. As indicated above, the function of p120 and p100 may also be regulated by their tyrosine phosphorylation, in which case appropriate modulation of kinases and phosphatases could modulate the function of cadherins and other cadherin-dependent processes.

p100 and p120 may be of utility in studying tumour cell invasion and metastasis, breast cancer, colorectal cancer, gastric carcinoma, gynaecological cancer, lung cancer, oesophageal cancer, prostate cancer, scirrhous cancer, and tissue regeneration, for example. Such studies could lead to diagnostic methods or treatments of these disorders.

The Drosophilia gene product *armadillo* is homologous to β-catenin and has been strongly implicated in developmental processes. It is therefore possible that p120 and p100, as β-catenin-related proteins that interact with cadherins, may also be involved in developmental defects and abnormalities.

The present invention also provides an agent which alters or blocks association between p100 or p120 with the catenin/cadherin complex of epithelial or endothelial cells for use in the treatment or diagnosis of a disease.

The disease may be tumour cell invasion and metastasis, breast cancer, colorectal cancer, gastric carcinoma, gynaecological cancer, lung cancer, oesophageal cancer, prostate cancer, scirrhous cancer, or tissue regeneration.

The agent may be used for the preparation of a medicament and may be used with a pharmaceutically acceptable carrier.

BRIEF DESCRIPTION OF THE DRAWINGS

The present invention will now be described by way of Example only with reference to the accompanying drawings, which are briefly described below:-

FIG. 9. Sequence analysis of peptides derived by LysC proteolysis of p100 from Caco-2 cells. Caco-2 cells(20× confluent 9 cm dishes) were lysed in TX buffer to minimize nuclear lysis. Insoluble protein was removed by centrifugation. Deoxycholate and SDS were added to the supernant to give (w/v) 0.5% and 0.2% final concentration, respectively. Addition of these detergents results in dissociation of p100 and p120 from the cadherin/catenin complex. p120 and p100 were immunoprecipitated from the lysate using the anti-p120 antibody (which also recognizes p100) from Transduction Laboratories, rabbit anti-mouse IgG and Protein A Sepharose. The immune complex was washed five times and then dissociated by the addition of Laemmli sample buffer followed by heating at 100° C. for 5 minutes. Proteins were precipitated by addition of four volumes of ethanol and incubation at −20° C. for 16 hours. The precipitate was resolved by SDS-PAGE (6% acrylamide) and proteins were visualized by Coomassie Blue. Protein corresponding to p100 was excised from the gel and digested with LysC. Peptides were separated by HPLC and sequenced. Mouse p120 sequence was described by Reynolds et al., 1992. Clearly, human p100 is closely related to mouse p120.

Figure 1A:
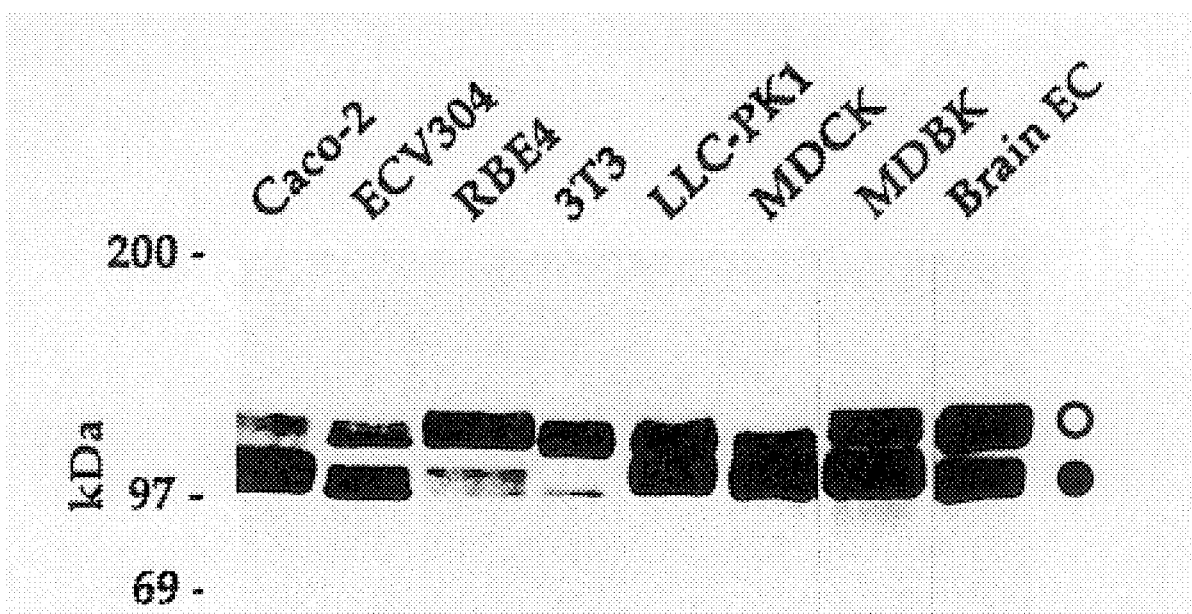
FIG. 1 (A–B). Characterization of anti-p120 and 2B12 immunoreactivity. Various cell lines and a primary culture of bovine brain endothelial cells (Brain EC) were lysed in SDS sample buffer and analyzed by SDS-PAGE followed by immunoblotting with anti-p120 antibody (Panel A) or the 2B12 antibody (Panel B). The exposure times were 1 minute for Panel A (apart from that for the MDBK cells which was 10 seconds) and 15 minutes for Panel B. The migration of p120 (○) and p100 (●) has been indicated.

In this figure the standard single letter amino acid code is used. Additionally "X" is used to designate any amino acid.

EXAMPLE

In the Examples given later the following materials and methods were used:-

Antibodies

The anti-canine E-cadherin antibody rr1 developed by Gumbiner and Simons (1986) was provided by Barry Gumbiner (Memorial Sloan-Kettering Cancer Center, N.Y.) or obtained from the Developmental Studies Hybridoma Bank maintained by the Department of Pharmacology and Molecular Sciences, Johns Hopkins University School of Medicine, Baltimore, Md. 21205, and the Department of Biological Sciences, University of Iowa, Iowa City, Iowa 52242, under contract N01-HD-2-3144 from the NICHD. The anti-human E-cadherin antibody HECD-1 (Shimoyama et al., 1989) was from Takara Biomedicals (Shiga, Japan). Anti-p120 and anti-focal adhesion kinase (FAKK) antibodies were from Transduction Laboratories (Lexington, Ky.). The anti-p120 antibody 2B12 (Kanner et al., 1990) was a gift from J. T. Parsons (University of Virginia, Charlottesville, Va.). The peptide-directed antibodies against α- and β-catenin (Staddon et al., J. Cell Sci. in press) were kindly provided by Kurt Herrenknecht (Eisai London Research) Laboratories Lt., University College London, London UK). All secondary antibodies used for immunoprecipitation and immunocytochemistry were from Jackson Laboratories Inc. (West Grove, Pa.). HRP-conjugated secondary antibodies used for immunoblotting were from Amersham (Bukinghamshire, UK).

Cells

The following cells were cultured at 37° C. in medium containing 100 U/ml penicillin and 100 μg/ml streptomycin: Caco-2 (epithelial cells derived from a human colonic tumour: 5% $CO_2$, M199, 10% FCS); LLC-PK1 (epithelial cells derived from porcine kidney: 5% $CO_2$, M199, 10% FCS); MDBK (epithelial cells derived from bovine kidney: 5% $CO_2$, MEM, 10% FCS); Strain 1 MDCK cells (epithelial cells derived from canine kidney: 5% $CO_2$, MEM, 10% FCS); RBE4 cells (immortalized rat brain endothelial cells (see Durieu-Trautmann et al., 1993): 5% $CO_2$, α-MEM: Ham's F10 (1:1), 10% FCS, 0.3 mg/ml geneticin, 1 ng/ml bFGF); Swiss 3T3 fibroblasts (10% $CO_2$, DMEM, 10% FCS). Caco-2, ECV304. LLC-PK1 and MDBK cells were obtained from the European Collection of Animal Cell Cultures (Salisbury, UK). MDCK cells were provided by Barry Gumbiner. RBE4 cells were from Pierre Couraud (Université Paris VII, Paris, France) and Swiss 3T3 fibroblasts were from Enrique Rozengurt (Imperial Cancer Research Fund, London, UK). Human umbilical vein endothelial cells were from Clonetics (Palo Alto, Calif.) and cultured according to the manufacturer's instructions. Primary cultures of bovine or porcine brain endothelial cells were grown as described by Rubin et al. (1991). For experimental purposes, confluent cultures of Caco-2, MDBK, MDCK and brain endothelial cells were established on tissue culture-treated, polycarbonate Transwell filters (polycarbonate, 0.4 μm; Costar, Cambridge, Mass.). Other cells were grown on tissue culture plastic.

Immunoblotting and Immunoprecipitation

Whole cell lysates from cultures maintained for 16–20 hours in 0.5% serum were prepared by rapidly replacing the medium with hot Laemmli sample buffer (Laemmli, 1970) supplemented with 5 mM EDTA, followed by heating at 100° C. for 5 minutes. Proteins were resolved by slab-gel electrophoresis as described by Laemmli, (1970). The gels were equilibrated in buffer containing 48 mM Tris, 39 mM glycine, 0.03% SDS (w/v) and 20% methanol (v/v), and then transferred to nitrocellulose filters (Hybond ECL, Amersham). After Ponceau S staining, the filters were blocked in 5% (w/v) non-fat dried milk in PBS at 4° C. for 16–18 hours. Filters were then incubated with primary antibody in PBS containing 0.05% Tween-20™ and 1% BSA, followed by detection with appropriate HRP-conjugated secondary antibody and chemiluminescence (ECL, Amersham).

Immunoprecipitations were performed at 4° C. Cultures were rinsed with PBS and then lysed in either TX buffer (1% (v/v) Triton X-100 ™, 25 mM Hepes, 2 mM EDTA, 0.1 M NaCl, 25 mM NaF, 1 mM vanadate, 25 µM phenylarsine oxide, pH 7.6 (adjusted with NaOH), 1 mM PMSF, 10 µg/ml soybean trypsin inhibitor, 0.1 U/ml $\alpha_2$-macroglobulin, 10 µg/ml leupeptin) or TDS buffer, which was identical to the TX buffer except that it was supplemented with 0.5% (w/v) sodium deoxycholate and 0.2% (w/v) SDS. The cells were incubated with lysis buffer for 10–15 minutes and then scraped. The lysates were collected and centrifuged at 14,000 x g for 20 minutes. The supernatant was precleared with Protein A sepharose ™ (Pharmacia, UK) for 1–2 hours and then incubated with primary antibody for 1 hour followed by a further 1 hour with Protein A Sepharose alone, in the case of rabbit antibodies, or together with rabbit anti-mouse antibodies for the mouse monoclonal antibodies. After five washes in lysis buffer, immune complexes were dissociated by addition of Laemmli sample buffer followed by heating at 100° C. for 5 minutes. Protein analysis was by SDS-PAGE and immunoblotting as described above.

For [$^{35}$S]methionine labelling, the cultures were washed twice in methionine-free MEM supplemented with 0.5% FCS. The cells were incubated for 16–18 hours in this medium containing 50 µCi/ml [$^{35}$S]methionine (>1000 Ci/mmol, Amersham). Protein analysis was by SDS-PAGE, followed by fixation in 25% methanol/10% acetic acid. Labelled protein was detected either by direct autoradiography at room temperature or by fluorography at −80° C. following impregnation of the gel with Amplify ™ (Amersham).

Immunocytochemistry

Cells were fixed at room temperature for 15 minutes in 3% paraformaldehyde made up in PBS containing 0.5 mM caCl$_2$ and 0.5 mM MgSO$_4$. Fixed cells were washed and then permeabilized by incubation with 0.5% Triton X-100™ in PBS for 10 minutes. After washing, the cells were incubated for 30 minutes in PBS containing 10% calf serum and 0.1 M lysine, pH 7.4. Incubation with primary antibody was in pBS containing 10% calf serum for 1 hour. After washing, the cells were then incubated for 30–60 minutes with a 1:100 dilution of fluorophore-conjugated anti-mouse or anti-rabbit IgG, as appropriate, in PBS containing 10% calf serum. After washing, the filters were mounted with Citifluor (Citifluor Products, Canterbury, UK) and examined using a Nikon™ Microphot-FXA™ fluorescence microscope fitted with 40 x and 60 x objectives. Photographs were taken using Kodak™ T-MAX film (400 ASA).

For the preparation of cryosections, brain and skeletal muscle from CO$_2$-asphyxiated rats were removed and rapidly frozen in liquid nitrogen. Tissue blocks were mounted in Tissue Tek (R. Lamb, London, UK) and sections of 5–10 µm thickness were cut on a Bright cryostat, air-dried and stored for up to 4 weeks at −20° C. After thawing, the sections were fixed and permeabilized as described above. The sections were then washed, blocked with PBS containing 10% calf serum for 15 minutes and incubated with primary antibody diluted in PBS containing 10% calf serum for 2 hours. After washing, they were incubated with PBS containing 10% calf serum with either 10% goat serum or 10% donkey serum, as appropriate for the host of the secondary antibody, for 15 minutes. They were then incubated with secondary antibody diluted in PBS and serum for 1 hour. Sections were washed, mounted and examined as described above.

EXAMPLE 1

Antibody Characterization: p120 and p100 Proteins

Figure 1B:
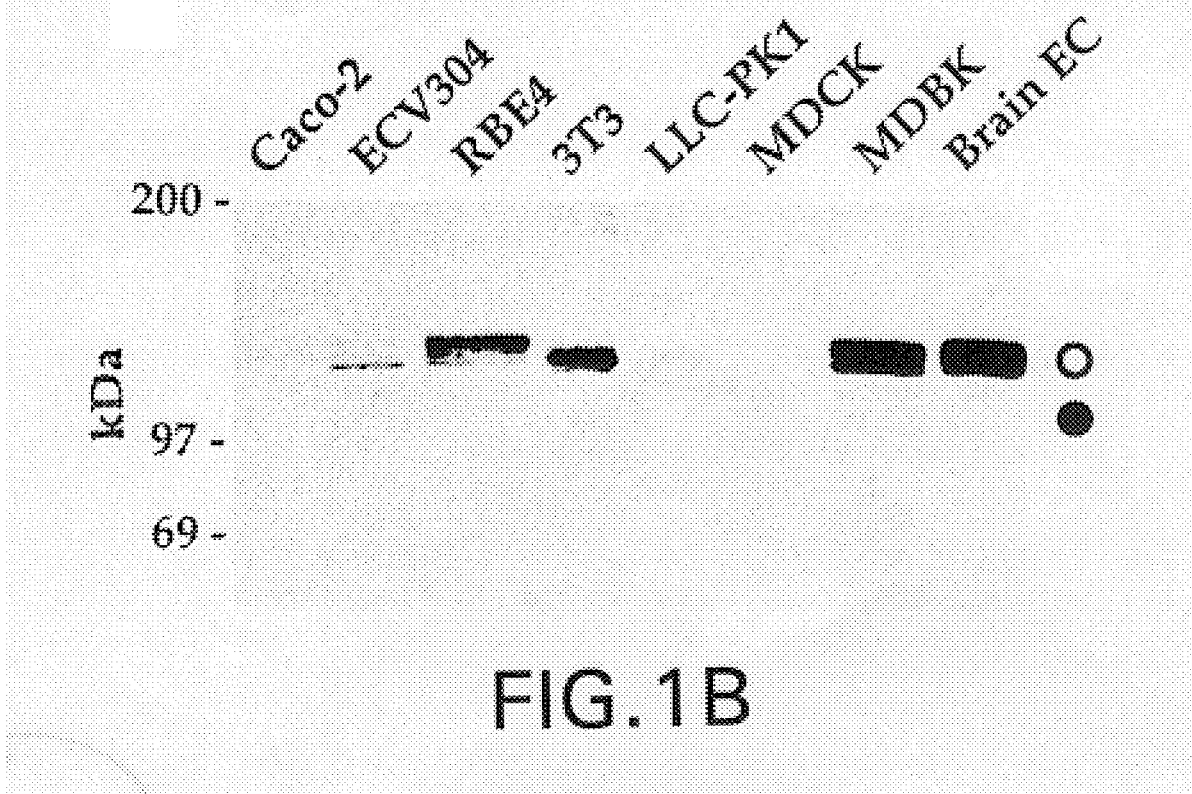

SDS lysates of a variety of cell types were analyzed by immunoblotting for expression of p120 using an anti-p120 antibody (FIG. 1 A). This antibody was raised against a fusion protein containing amino acids 790–911 at the C-terminus of p120. The antibody clearly reacted with two distinct bands of apparent molecular mass 120 kDa and 100 kDa in extracts of Caco-2, ECV 304. RBE4, Swiss 3T3, LLC-PK1. MDBK and brain endotheiial cells. We will hereafter refer to these two bands as p120 and p100. With the MDCK cells a broad continuous band was detected. The relative intensity of the staining of p120 and p100 depended on the cell type. For example, p100 was more intense than p120 in Caco-2 cells and in the Swiss 3T3 cells the reverse was observed. These blots were also probed with the monoclonal anti-p120 antibody 2B12, raised against a phosphotyrosine immunoprecipitate prepared from pp60$^{src}$ transformed chicken embryo fibroblasts (Kanner et al., 1990). This antibody recognised only the upper of the two bands (FIG. 1 B). 2B12 reacted strongly with bovine protein, moderately with rodent protein and weakly with human protein. However, it failed to react with extracts of the LLC-PK1 (porcine) and MDCK (canine) cells, reflecting limited cross-species reactivity.

Figures 2A, 2B:
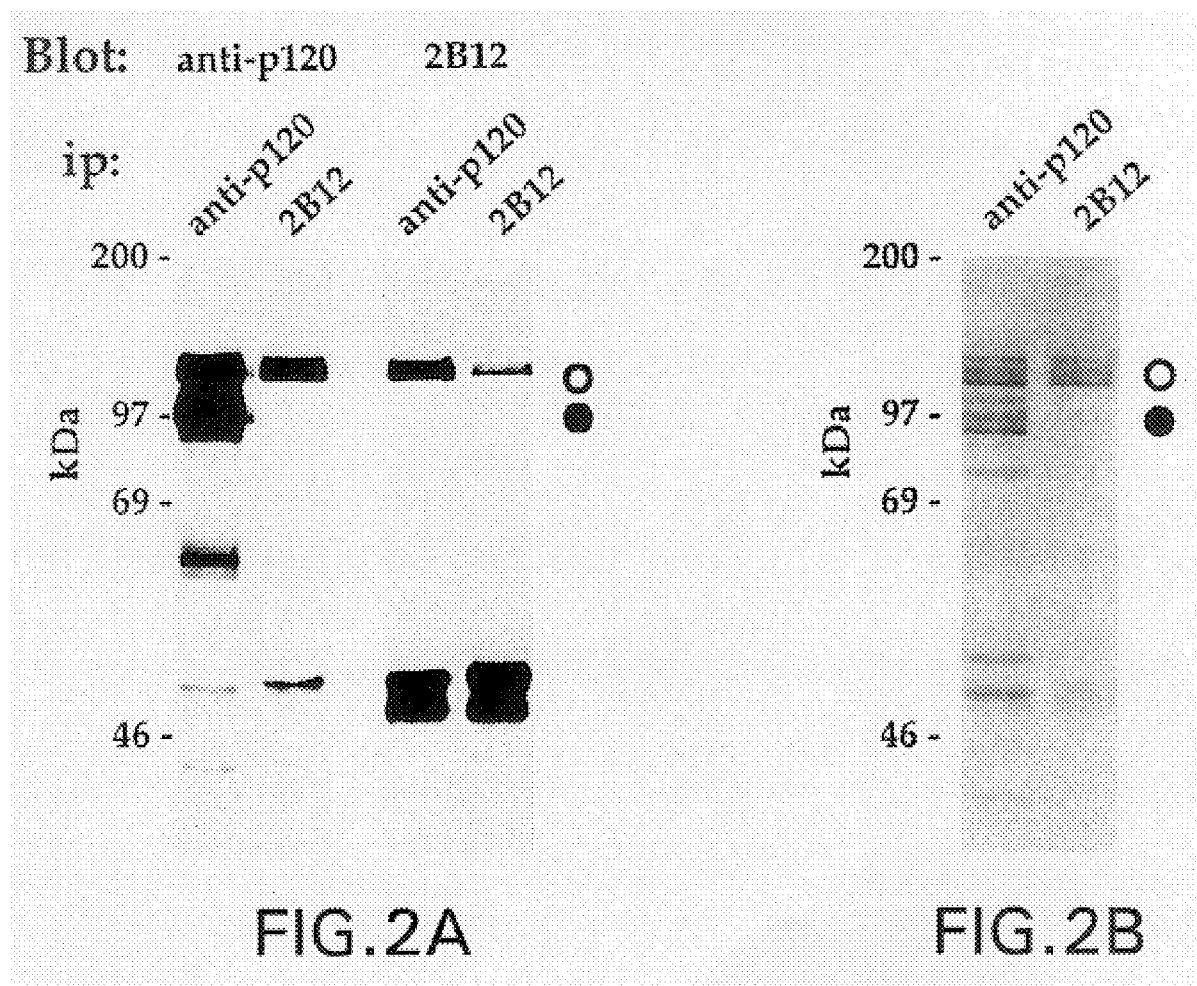
FIG. 2 (A–B). p120 protein is recognized by the anti-p120 antibody and cross-reacts with the 2B12 antibody, whereas p100 is recognized only by anti-p120. MDBK cells were lysed in TDS buffer. Immunoprecipitations were performed using the anti-p120 antibody or 2B12 followed by cross-blotting (Panel A). MDBK cells were chosen because p120 and p100 are well separated by SDS-PAGE and react with both antibodies. In Panel B, MDBK cells were labelled with [$^{35}$S]methionine, lysed in TDS buffer and then immunoprecipitated using anti-p120 or 2B12. Proteins were separated by SDS-PAGE and detected by autoradiography. Clearly, the broad bands(Panel A and see FIG. 1 A) corresponding to p120 and p100 as detected by immunoblotting are resolved as multiple bands. The same bands as seen in the 2B12 immunoprecipitate (○) are seen in the anti-p120 immunoprecipitates. In the anti-p120 immunoprecipitates, additional bands (●) corresponding to p100 are also observed.

The relationship between the known pp60$^{src}$ substrate p120 and p100 was further examined by immunoblot analysis of immunoprecipitates from cells lysed. in TDS buffer, used to minimize protein-protein interaction (FIG. 2A). MDBK cells were used since both the anti-p120 and 2B12 antibodies worked well (FIG. 1). In the anti-p120 immunoprecipitates, p120 and p100 were detected by blotting with the anti-p120 antibody. 2B12 only reacted with p120 in these immunoprecipitates. In 2B12 immunoprecipitates, blotting with both 2B12 and the anti-p120 antibody revealed p120. Thus, 2B12 recognized p120, whereas the anti-p120 antibody recognized the same p120 protein as 2B12 and, in addition, a p100 protein.

Autoradiographic analysis of immunoprecipitates of [$^{35}$S] methionine-labelled MDBK cells, as resolved by SDS-PAGE (FIG. 2B), revealed that the p120 protein migrated as a cluster of bands that were identical in the both 2B12 immunoprecipitates and the anti-p120 immunoprecipitates. However, in the anti-p120 immunoprecipitates a similar cluster of additional bands corresponding to p100 was detected. Technically, detection by immunoblotting was light based (chemiluminescence) which does not have the greater resolution of direct autoradiography, hence the multiple bands seen in FIG. 2B appear as a broad band in FIG. 2A. The basis of the multiplicity of the bands corresponding to p120 and p100 in the MDBK cells is not clear. However, [$^{32}$P]phosphate-labelling of these cells raised the possibility that these bands may represent differentially phosphorylated protein (results not shown).

Association with the Cadherin/Catenin Complex: Epithelial Cells

Figure 3A:
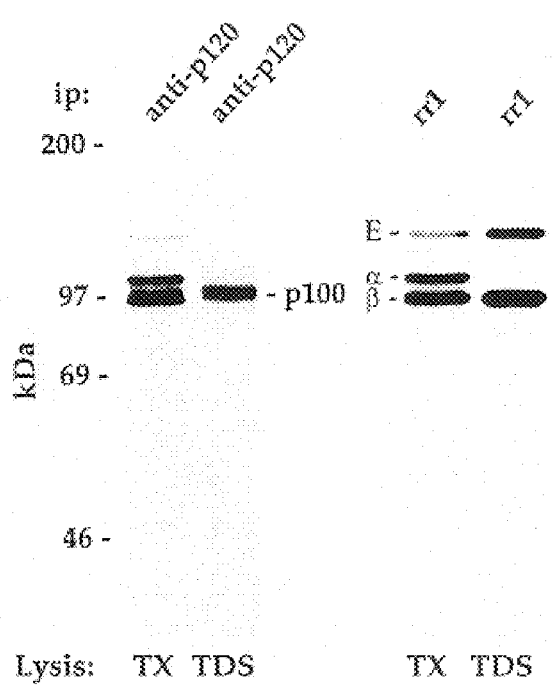
FIG. 3 (A–B). Comparison of anti-p120 and anti-E-cadherin immunoprecipitates from MDCK and Caco-2 cells. Panel A: MDCK cells were labelled with [$^{35}$S]methionine and then lysed in either TX buffer or TDS buffer. Immunoprecipitations were performed using anti-p120 or anti-E-cadherin (rr1). Proteins were separated by SDS-PAGE followed by fluorography. Bands corresponding to E-cadherin (E), α-(α) and β-catenin (β) which are seen strongly in the rr1 immunoprecipitates have been indicated. The major anti-p120 reactive band migrates at approximately the position of that of p100 (see FIG. 1 A). 2B12 does not appear to react with canine protein (see FIG. 1 B) making positive identification of p120 difficult. Panel B: Caco-2 cells were labelled with [$^{35}$S]methionine and then lysed in TX buffer. Immunoprecipitations were performed using anti-E-cadherin (HECD-1), anti-β-catenin or anti-p120 antibodies. Proteins were separated by SDS-PAGE followed by fluorography. In all cases, four major comigrating bands were immunoprecipitated, corresponding in order of increasing mobility to E-cadherin, α-, β- and γ-catenin.

We next examined the possibility of association of p120 or p100 with other proteins. When TDS lysates of [$^{35}$S] methionine-labelled MDBK cells were immunoprecipitated wit the anti-p120 antibody, p120 and p100 were isolated as the major proteins corresponded to those detected by immunoblotting (FIG. 2). Similarly, the major bands seen in immunoprecipitates from TDS lysates of [$^{35}$S]methionine-labelled MDCK cells corresponds to the broad band detected by immunoblotting (cf. FIG. 1A and FIG. 3A). In contrast, the anti-p120 immunoprecipitates from MDCK cells lysed in TX buffer, used to preserve macromolecular protein complexes, revealed additional distinct bands at approximately 130 kDa, 105 kDa and 97 kDa (FIG. 3A). Proteins of similar molecular mass were seen in E-cadherin immunoprecipitates from similarly lysed cells (FIG. 3A). In this case, the 130 kDa band corresponds to E-cadherin, the 97 kDa band to β-catenin, and the 105 kDa band to α-catenin, which is dissociated from the complex by lysis in TDS buffer (see McCrea and Gumbiner, 1991). Thus, it appeared that the anti-p120 antibody may be capable of immunoprecipitating the cadherin/catenin complex.

Figure 3B:
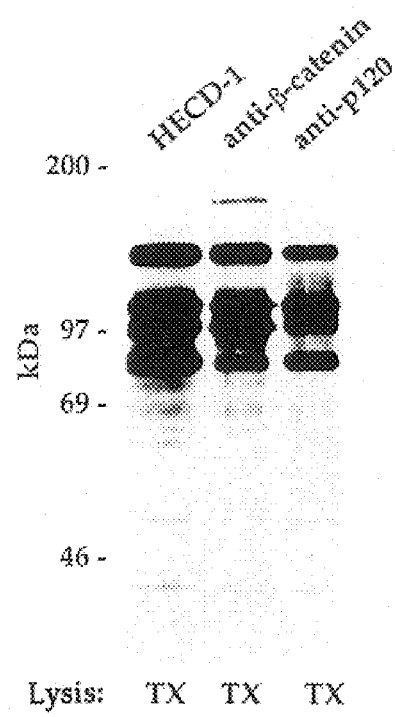

Caco-2 cells were also [$^{35}$S]methionine-labelled, lysed in TX buffer and immunoprecipitations were performed using the anti-E-cadherin antibody HECD-1, anti-β-catenin antibody or the anti-p120 antibody. HECD-1 or anti-β-catenin clearly immunoprecipitated four major bands corresponding in order of increasing mobility to E-cadherin, α-,β-, and γ-catenin. Similar bands were immunoprecipitated, but to a lesser extent, with the anti-p120 antibody (FIG. 3B). These results (not shown) were also obtained in MDBK cells when β-catenin immunoprecipitates were compared with those obtained with the anti-p120 antibody. Thus, it appears that the anti-p120 antibody can immunoprecipitate proteins that comigrate with those of the cadherin/catenin complex from a variety of epithelial cell lines.

Figure 4:
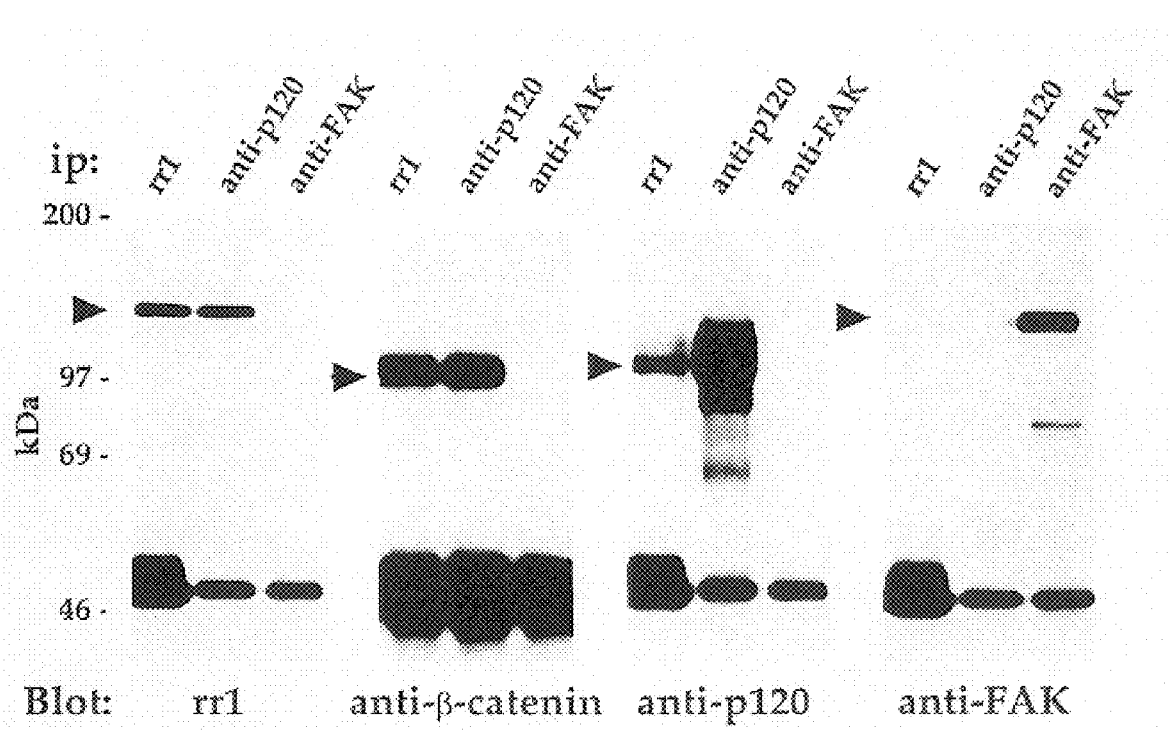
FIG. 4. Detection of anti-p120 reactive materials in anti-E-cadherin immunoprecipitates and E-cadherin in the anti-p120 immunoprecipitates. MDCK cells were lysed in TX buffer. Immunoprecipitations were performed with either antibody to E-cadherin (rr1), the anti-p120 antibody or anti-focal adhesion kinase (anti-FAK). A sham immunoprecipitation was performed in the absence of primary antibody (-). Following separation by SDS-PAGE, parallel blots were probed using: rr1 (arrowhead, E-cadherin); anti-β-catenin (arowhead, β-catenin); anti-p120 (arrowhead, anti-p120 reactivity); anti-FAK (arrowhead, FAK). Clearly, rr1 and the anti-p120 antibody immunoprecipitated E-cadherin and β-catenin. rr1 could also immunoprecipitate anti-p120 immunoreactive material, but to a lesser extent than that immunoprecipitated by the anti-p120 antibody. Anti-FAK could only immunoprecipitate FAK, and the sham immunoprecipitation did not result in any detectable E-cadherin, β-catenin or anti-p120 reactive material.

The comigration of bands in the anti-p120 and anti-E-cadherin immunoprecipitates suggests, but does not prove, that anti-p120 is capable of immunoprecipitating the cadherin/catenin complex. Therefore, the identity of the proteins in the E-cadherin and anti-p120 immunoprecipitates was examined by immunoblotting (FIG. 4). As expected, E-cadherin and β-catenin were both present in the rr1 immunoprecipitates. An anti-p120 reactive band displaying a mobility that was similar to that of β-catenin was also present in the rr1 immunoprecipitates. In the anti-p120 immunoprecipitates, anti-p120 reactive material was also present, unsurprisingly, but to a greater extent and migrated as a broader band than that seen in the rr1 immunoprecipitates. In the anti-p120 immunoprecipitates, E-cadherin and β-catenin also were clearly detected. Omission of primary antibody did not result in E-cadherin, anti-p120 reactivity or β-catenin in the immunoprecipitates. Immunoprecipitation with anti-FAK antibody, of the same species and isotype as the anti-p120 antibody, immunoprecipitated FAK but not E-cadherin, β-catenin or anti-p120 reactivity (FIG. 4).

It should be noted that although β-catenin and the anti-p120 immunoreactive band seen in the anti-E-cadherin immunoprecipitates have a similar mobility (FIG. 4), this does not represent cross-reactivity of the anti-p120 antibody with β-catenin. Thus, in β-catenin immunoprecipitates from MDCK cells lysed in TDS buffer, which resulted in dissociation of anti-p120 reactive material from the complex of β-catenin and E-cadherin (see FIG. 3A), the anti-p120 antibody failed to react with β-catenin. Conversely, anti-p120 immunoprecipitates from TDS lysed cells fail to contain 3-catenin immunoreactivity (results not shown). We also observed the anti-p120 immunoreactive band, as seen in the rr1 immunoprecipitates (FIG. 4), in α-catenin and β-catenin immunoprecipitates (results not shown).

Therefore, on the basis of the comigration of [$^{35}$S] methionine-labelled bands seen in anti-E-cadherin and anti-p120 immunoprecipitates of cells lysed in TX buffer, it appeared that the anti-p120 antibody could immunoprecipitate the cadherin/catenin complex. By immunoblotting, the unequivocal identification of E-cadherin and β-catenin in the anti-p120 immunoprecipitates verified this interpretation.

Example 2

Association with the Cadherin/Catenin Complex: Endothelial Cells

Figure 5:
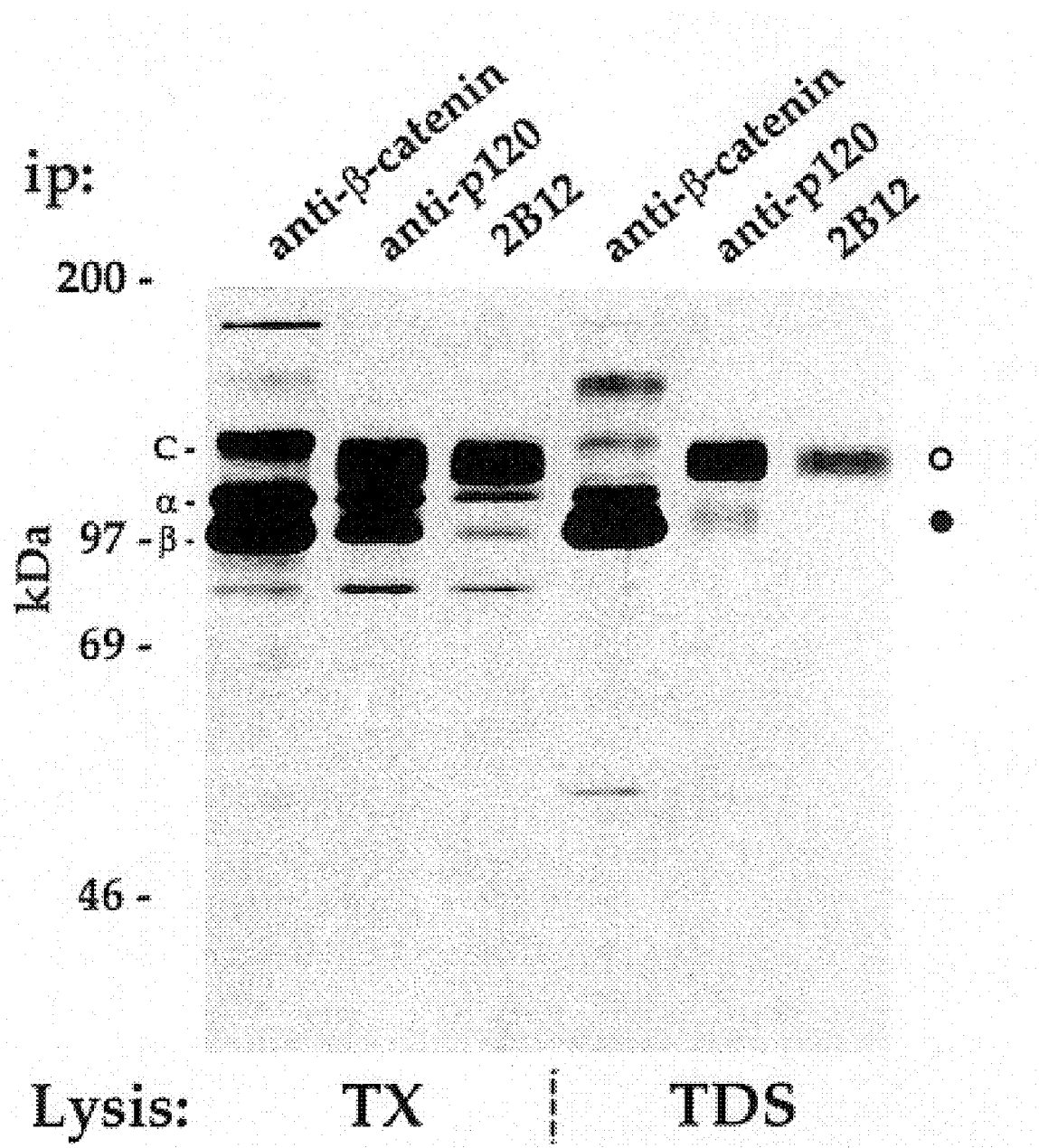
FIG. 5. Comparison of anti-β-catenin, anti-p120 and 2B12 immunoprecipitates from primary cultures of bovine brain endothelial cells. Cells were labelled with [$^{35}$S] methionine and then lysed in TX buffer or TDS buffer. Immunoprecipitations were performed using anti-β-catenin, anti-p120 and 2B12. Proteins were separated by SDS-PAGE followed by fluorography. In the β-catenin immunoprecipitation from TX lysed cells, bands corresponding to a cadherin (C), α-catenin (α) and β-catenin (β) have been indicated. Under TDS conditions, a band (○) corresponding to p120 is seen in the anti-p120 and 2B12 immunoprecipitates and a further band (●) is only seen in the anti-p120 immunoprecipitate, corresponding to p100.

Endothelial cells form junctional complexes of similar composition to those found in epithelial cells (for review, see Rubin, 1992). As shown (FIG. 1), endothelial cells also contain p120 and p100 proteins. We therefore asked whether p100/p120 is also associated with the cadherin/catenin complex in endothelial cells. Brain endothelial cells were labelled with [$^{35}$S]methionine, lysed with TX buffer and immunoprecipitated with either anti-β-catenin antibody, anti-p120 antibody or, because of its strong reactivity against bovine protein (see FIG. 1), 2B12. The anti-β-catenin antibody clearly immunoprecipitated three major proteins (FIG. 5), corresponding in order of increasing mobility to a 120–130 kDa band, probably representing a cadherin, and α-(105 kDa) and β-catenin (97 kDa). The anti-p120 antibody immunoprecipitated proteins (but to a lesser extent than those observed in the β-catenin immunoprecipitates) that comigrated with α- and β-catenin and a broad 120 kDa band, representing p120 (see later), that migrated between the presumptive cadherin and α-catenin (FIG. 5). In the 2B12 immunoprecipitates, proteins that comigrated with α- and β-catenin were also observed but to a much lesser extent than observed in the β-catenin immunoprecipitates. Again, a broad 120 kDa band was observed in these immunoprecipitates. From TDS lysates, anti-β-catenin antibody could still precipitate β-catenin, but anti-p120 antibody failed to do so. Instead, a diffuse band was observed that migrated slightly more slowly than β-catenin, and this was absent in the 2312 immunoprecipitates, therefore representing p100. In the 2B12 immunoprecipitates, only the 120 kDa band was observed. Thus, association between the catenins and p120 or p100 appeared to be observed in TX lysates, but not TDS lysates, of brain endothelial cells.

Figure 6A:
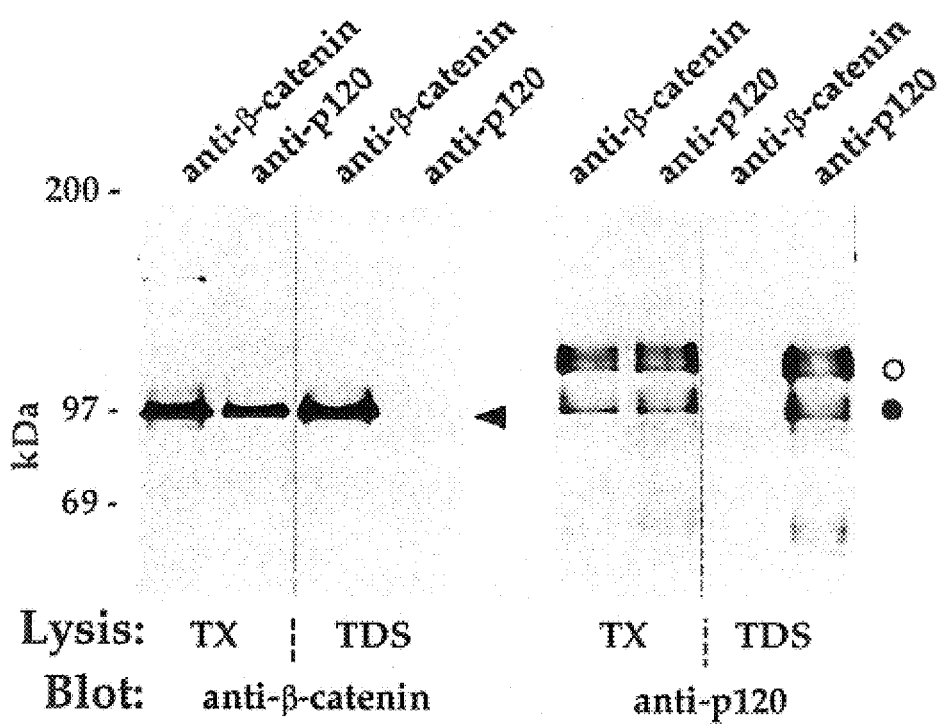
FIG. 6 (A–D). Detection of p120/p100 in β-catenin immunoprecipitates and β-catenin in anti-p120 immunoprecipitates from human umbilical vein endothelial cells (Panel A) and ECV304 cells (Panel B). Cells were lysed in either TX or TDS buffer. Lysates were immunoprecipitated using anti-β-catenin or the anti-p120 antibody, followed by analysis by SDS-PAGE and immunoblotting. The migration of β-catenin (arrowheads), p100 (●) and p120 (○) have been indicated. Note the absence of anti-p120 reactive material in the β-catenin immunoprecipitates obtained using TDS buffer. Even though β-catenin and p100, as defined by its reactivity with anti-p120 antibody, migrate very closely, they are clearly distinct proteins.
Figure 6B:
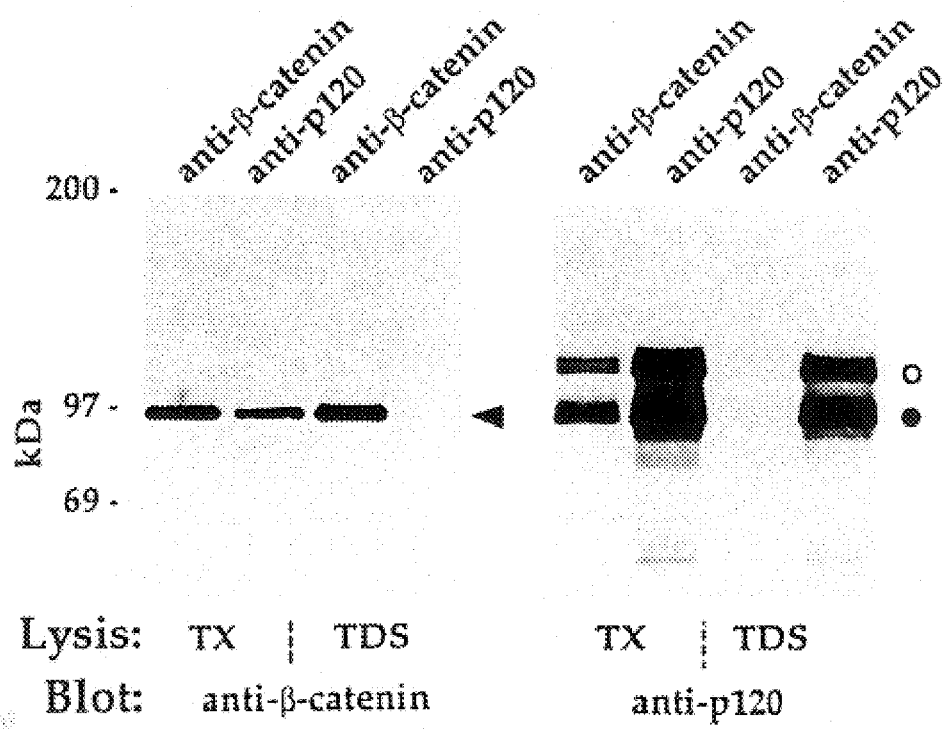

To explore the generality of these observations, similar experiments were performed using human umbilical vein endothelial cells (FIG. 6A) and ECV304 cells (FIG. 6B) but using immunoblot analysis. Thus, from cells lysed in TX buffer, anti-β-catenin antibody immunoprecipitated β-carenin, as expected, but also two bands of anti-p120 immunoreactivity, corresponding to p100 and p120. Similarly, the anti-p120 antibody immunoprecipitated p100 and p120l, as expected, and β-catenin. However, as for the brain endothelial cells and the epithelial cells, TDS buffer resulted in dissociation of β-catenin and p100/p120. These data corroborate those obtained from the analysis of the immunoprecipitates from [$^{35}$S]methionine-labelled brain endothelial cells (FIG. 5).

Example 3

Localization of Cell-Cell Junctions

Figure 7A:
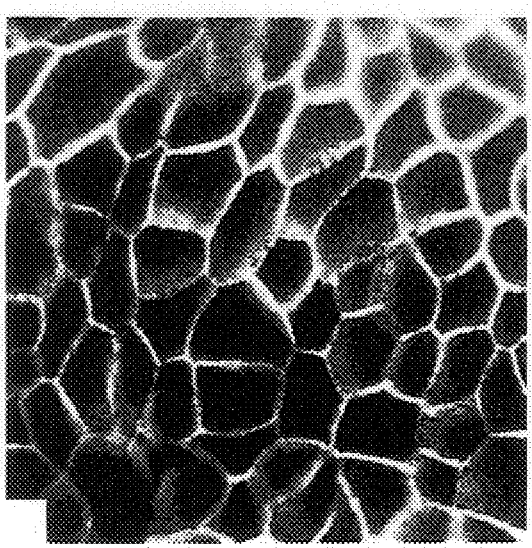
FIG. 7 (A–B). Localization of anti-p120 reactivity and β-catenin in MDCK cells, and brain endothelial cells. MDCK cells (Panel a, b) and porcine brain endothelial cells (Panel c, d) were co-labelled with anti-p120 antibody (Panel a, c) and anti-β-catenin antibody (Panel b, d). Secondary antibodies were fluorescein-conjugated anti-mouse and rhodamine-conjugated anti-rabbit. In this instance, it was verified that each secondary antibody was absolutely specific for its designated species of primary antibody. Bar: 20 μm.
Figure 7B:
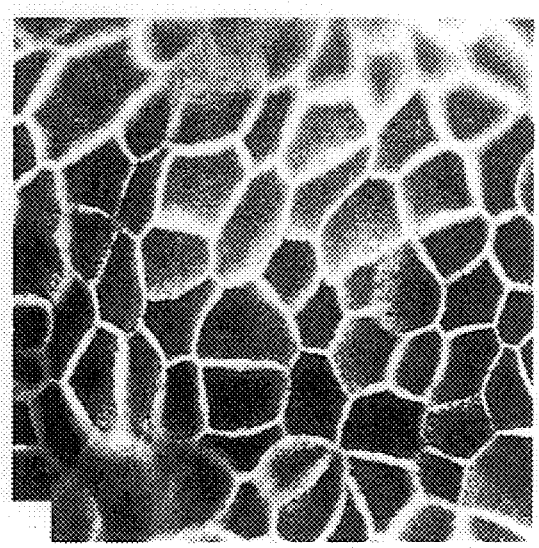
Figure 7C:
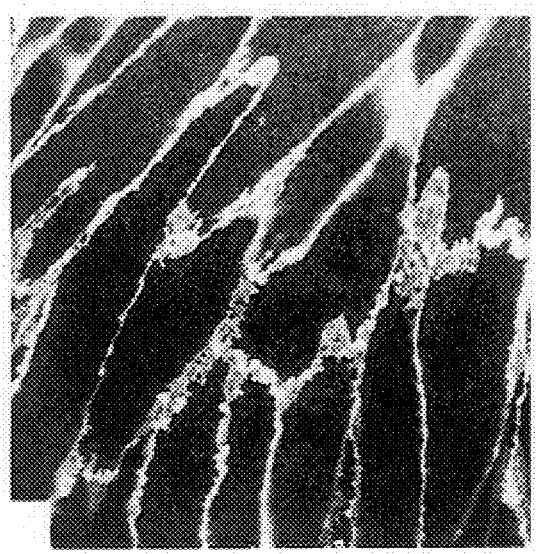
Figure 7D:
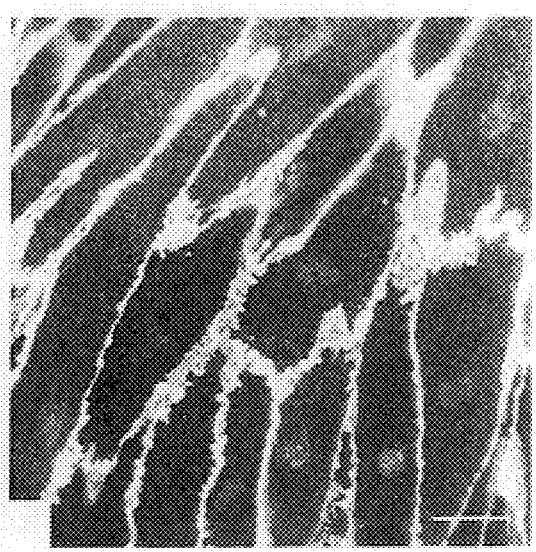
Figure 8A:
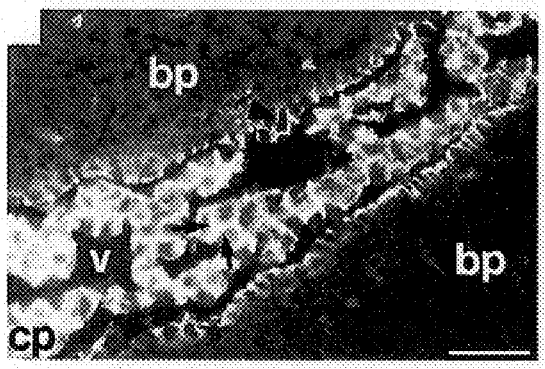
FIG. 8 (A–H). Distribution of anti-p120 immunoreactivity in brain and skeletal muscle tissue of the rat. Brain tissue was co-labelled with the anti-p120 antibody (a, c) and anti-α-catenin (b, d). Anti-p120 immunoreactivity and α-catenin co-localise at intercellular junctions of choroid plexus epithelium (arrows, a and b) and ventricular ependymal cells (arrowheads, a and b). Both antigens also co-localise at interendothelial junctions of blood vessels of macrovascular origin(arrows in c and d). Microvascular profiles in brain sections were identified by labelling with anti-collagen IV antibody (f); co-labelling with the anti-p120 antibody (e), revealed the presence of antigen at interendothelial junctions (e, arrows). In these microvessels, α-catenin co-localised with anti-p120 immunoreactivity (not shown). In muscle tissue which had been cut perpendicular to the orientation of the muscle fibres, anti-p120 immunoreactivity is limited to areas between muscle fibres where blood vessels are located(g, arrows). Higher magnification reveals a punctate staining pattern (h, arrows) which is likely to reflect anti-p120 immunoreactivity at interendothelial junctions. In Panels a, c and e, bp depicts the brain parenchyma; in Panel a, v the ventricular lumen and cp the choroid plexus; in Panel g, m refers to muscle tissue. Bars: (a, g), 100 μm; (c, e, h), 25 μm.
Figure 8B:
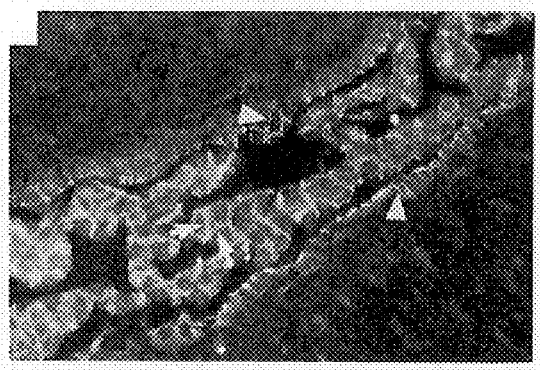
Figure 8C:
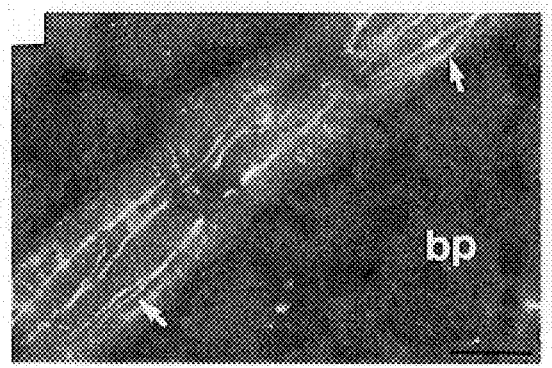
Figure 8D:
Figure 8E:
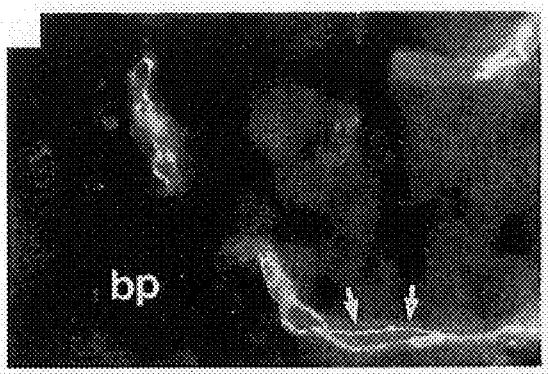
Figure 8F:
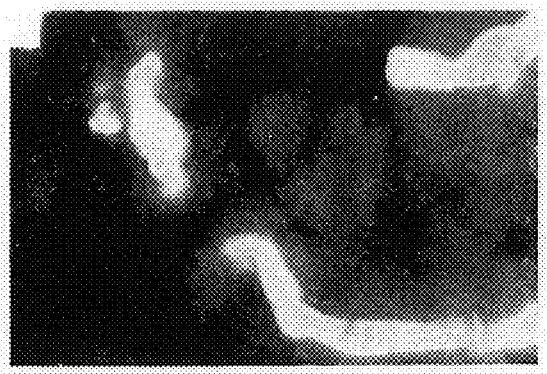
Figure 8G:
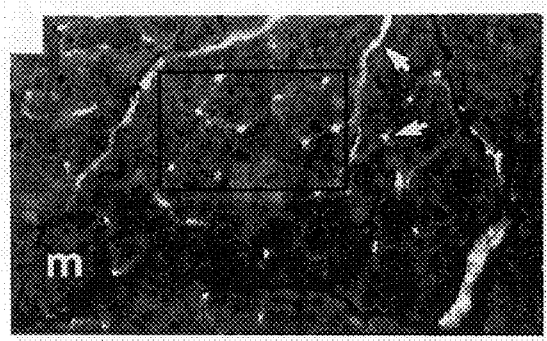
Figure 8H:
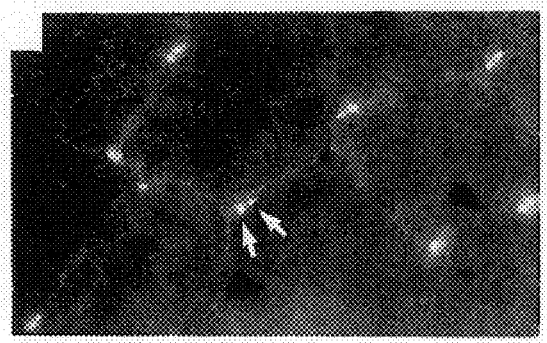

To investigate the cellular localization of p100/p120, immunocytochemical analysis was performed. Unfortunately, 2B12 did not label cells under the fixation conditions that were tried (paraformaldehyde and methanol). However, the anti-p120 antibody (which recognizes p120 and p100) stained cells well. Double-labelling of MDCK cells with anti-β-catenin and the anti-p120 antibody revealed a striking co-localization of β-catenin and anti-p120 immunoreactivity (FIG. 7a,b). Similar results were found for the brain endothelial cells (FIG. 7c,d).

Immunocytochemistry was further performed on frozen sections of brain and skeletal muscle (FIG. 8). Anti-p120 immunoreactivity co-localized with α-catenin at intercellular junctions of choroid plexus epithelium and ventricular ependymal cells (FIG. 8a,b). In addition, the anti-p120 antibody stained inter-endothelial junctions in both large (FIG. 8c,d) and small blood vessels of the brain (FIG. 8e,f) and blood vessels of muscle tissue (FIG. 8g,h). At the given detection level, anti-p120 immunoreactivity was limited to endothelial and epithelial cells in the two types of tissue investigated.

In the present study, immunoblot analysis of a variety of different cells revealed that the anti-p120 monoclonal antibody 2B12 (Kanner et al., 1990) recognized a broad band of approximately 120 kDa. Another anti-p120 monoclonal antibody that had been raised against the C-terminal portion of p120 recognized the same bands as 2B12 and, in addition, another cluster of bands at 100 kDa. The reason for the multiplicity of bands at 120 kDa and 100 kDa is not clear, but obviously they are immunologically related. The pattern of appearance of these multiple bands also depended on the cell type. For example in MDCK cells the bands were very diffuse, whereas in MDBK cells they were clearly resolved, especially when visualized by [$^{35}$S]methionine labelling in the absence of fluorographic reagent. It is possible that post-translational modification, such as phosphorylation and myristoylation may account for the appearance of multiple bands. The relationship, apart from the immunological one, between p120 and p100 is not yet clear. The Northern blots described by Reynolds et al. (1992) suggested the possibility of p120-related gene products or alternatively spliced transcripts. Furthermore, Southern analysis apparently indicated that one or more p120-related genes exit (Reynolds et al., 1992). It follows that the cluster of bands corresponding to p120 and the similar cluster to p100 could also represent splice variants of, respectively, p100 and p120. It is also possible that p100 could simply represent a degradation product of p120, although samples were prepared in denaturing buffer and immunoprecipitations were performed in the presence of inhibitors of a broad spectrum of proteases.

Our results provide evidence that p120/p100 associates with the cadherin/catenin complex. Thus, from TX-solubilized epithelial cells, anti-p120 antibody immunoprecipitated [$^{35}$S]methionine-labelled proteins that comigrated with those immunoprecipitated by cadherin antibodies (FIG. 3). Immunoblot analysis verified the identity of these proteins as cadherins and catenins (FIG. 4). Similarly, anti-p120 reactive protein was seen in the anti-E-cadherin immunoprecipitates from MDCK cells, although on the basis of mobility this appears to represent primarily p100, not p120 (FIG. 4). However, it should be noted that p120 immunoreactive protein was not unequivocally identified in the MDCK cells because of the poor reactivity of the 2B12 antibody with canine protein. This apparent association between p120/p100 and the cadherin/catenin complex was not restricted to epithelial cells as similar results were obtained using endothelial cells, both by [$^{35}$S]methionine-labelling (FIG. 5) and immunoblot analysis (FIG. 6). However, although our results clearly show an interaction between catenins and p120/p100 in endothelial cells, we did not identify a cadherin in the anti-p120 immunoprecipitates. The interpretation of the biochemical analyses of the protein complexes in the epithelial and endothelial cells is further supported by the immunocytochemical study. In cultured cells and in tissue sections, anti-p120 immunoreactivity was strongly associated with intercellular junctions, displaying a localization that was remarkably similar to that obtained with anti-β-catenin antibody (FIGS. 7 and 8). Here, we were restricted to using the anti-p120 antibody which might recognize either p120 or p100, or both.

Of course, one explanation for the ability of anti-p120 antibody to immunoprecipitate the cadherin/catenin complex is that it cross-reacts with one of the known components of the complex. However, this is unlikely for the following reasons. TDS lysis of cells dissociates α-catenin and γ-catenin from the cadherin and β-catenin complex (see McCrea and Gumbiner, 1991). In anti-E-cadherin immunoprecipitates from MDCK cells lysed in TDS buffer, anti-p120 antibody failed to react with E-cadherin or the co-precipitating β-catenin. In anti-α-catenin immunoprecipitates from MDCK cells lysed in TDS buffer, anti-p120 antibody failed to react with α-catenin (results not shown). As shown in FIG. 6, β-catenin immunoprecipitates from TDS-lysed endothelial cells, although clearly containing β-catenin, and presumably a cadherin, did not contain any anti-p120 reactivity. Cross-reactivity with γ-catenin, a protein of approximately 85 kDa, is unlikely as the immunoblots shown in FIG. 1 fail to show reactivity with protein below 100 kDa.

One problem that has to be addressed concerns the lack of any obvious [$^{35}$S]methionine-labelled bands that correspond to p120/p100 in the cadherin immunoprecipitates from TX lysed cells. Thus, as shown in FIG. 3, rr1 and the anti-p120 immunoprecipitates from MDCK cells look remarkably similar. However, it is clear from the anti-p120 immunoprecipitates from TDS lysed cells that the anti-p120 reactive material migrates as a broad band, the bulk of which migrates between α- and β-catenin, with the remainder migrating slightly slower than α-catenin. In conjunction with the immunoblot analysis shown in FIG. 4, which demonstrates that only a fraction of the anti-p120 immunoreactive material is immunoprecipitated by rr1, and the fact that p120 contains about half of the number of methionines in α- and β-catenin, if we assume steady-state labelling, then it is obvious that it would be difficult to see any labelling corresponding to the anti-p120 immunoreactive material in the rr1 immunoprecipitates. Similarly, with respect to the experiments with the brain endothelial cells (FIG. 5), under the extraction conditions employed it appears that only a fraction of the pool of the cadherin/catenin complex associates with p100, and even less with p120. Thus, it would be difficult to see labelling of bands corresponding to p120 and p100 in the β-catenin immunoprecipitates as this region of the gel is already occupied by other major bands. It is also difficult to discern a band corresponding to the cadherin seen in the β-catenin immunoprecipitates in either the anti-p120 or 2B12 immunoprecipitates because of the dominance of the labelling of p120 (FIG. 5).

We emphasize that there are also clear quantitative differences with respect to the ability of 2B12 and anti-p120 antibody to immunoprecipitate the cadherin/catenin complex. Due to poor reactivity of 2B12 with canine protein, this could not be addressed with MDCK cells. In bovine brain endothelial cells, the anti-p120 antibody immunoprecipitated the cadherin/catenin complex, although not as well as anti-β-catenin antibody. 2B12 was even less effective than anti-p120. As anti-p120 recognizes p120 and p100, and 2B12 only p120, the difference in the amount of the complex immunoprecipitated must be attributable to greater association of p100 with the catenins. As far as we can tell, the efficiency of anti-p120 and 2B12 in immunoprecipitation was similar in this experiment (see FIG. 5 for the similar intensity of a band corresponding to p120 in the anti-p120 and 2B12 immunoprecipitates from cells lysed in TX buffer). These data also indicate that independent complexes of p100 and p120 exist with catenins, rather than a catenin/p100/p120 complex. If the latter were the case, 2B12 would be expected to immunoprecipitate as much of the catenins as anti-p120 antibody.

Our study provides a link between p120/p100 and adherens junction proteins. It is possible that such an interaction, perhaps via the influence of regulatory kinases, such as src, lyn and yes (see Tsukita et al., 1991), may play a role in the modulation of cadherin function, and thereby other cellular functions influenced by the adherens junction. With respect to phosphorylation, the tyrosine phosphatase inhibitor phenylarsine oxide was found to cause an increase in tight junction permeability in MDCK cells (Staddon et al., *J. Cell Sci.* in press). This inhibitor increased the tyrosine phosphorylation of the anti-p120 immunoreactive material (a major p100 band, a minor p120 band) in these cells, as analyzed by anti-p120 immunoblotting of anti-p120 immunoprecipitates from SDS lysates (results not shown; see Staddon et al., *J. Cell Sci.* in press). The p120/p100 proteins could also be involved in the interaction between cadherins and the actin-based cytoskeleton. p120/p100 may also be part of a signalling cascade, communicating information about the state of cell-cell adhesiveness to the interior of the cell.

β-catenin is an arm protein (McCrea et al., 1991) and can associate with cadherins and the APC gene product (Rubinfeld et al., 1993; Su et al., 1993), also an arm protein (see Peifer et al., 1994). p120 is an arm protein (Reynolds et al., 1992; Peifer et al., 1994), and, as we describe here, p100 is an immunologically related protein. These proteins can interact with β-catenin. The exact nature of the interaction between p120/p100 and the catenins remains to be established. These proteins may interact directly, or associate with different regions of the cytoplasmic domain of cadherins. Other linking or intermediary binding proteins could also be involved. Clearly, there appears to be diverse interactions among arm proteins, suggesting the importance of the arm motif in intracellular signalling.

In summary, our studies identify p100 as a p120-related protein. We present evidence that these proteins interact with the cadherin/catenin complex. Given the important role of the cadherin/catenin complex in cellular transformation and the identification of p120 as a pp60$^{src}$ substrate, this suggests that p120/p100 may play a role in cellular growth control and other processes, such as tight junction permeability control, via an influence on cell-cell adhesion.

REFERENCES

Behrens, J., M. M. Mareel, F. M. Van Roy, and W. Birchmeier. 1989. Dissecting tumor cell invasion: epithelial cells acquire invasive properties after the loss of uvomorulin-mediated cell-cell adhesion. *J. Cell Biol.* 108:2435–2447.

Birchmeier, W., and J. Behrens. 1994. Cadherin expression in carcinomas: role in the formation of cell junctions and the prevention of invasiveness. *Biochim. Biophys. Acta.* 1198:11–26.

Boller, K., D. Vestweber, and R. Kemler. 1985. Cell-adhesion molecule uvomorulin is localized in the intermediate junctions of adult intestinal epithelial cells. *J. Cell Biol.* 100:327–332.

Downing, J. R., and A. B. Reynolds. 1991. PDGF, CSF-1, and EGF induce tyrosine phosphorylation of p120, a pp60$^{src}$ transformation-associated substrate. *Oncogene.* 6:607–613.

Durieu-Trautmann, O., C. Fédérici, C. Créminon, N. Foignant-Chaverot, F. Roux, M. Claire, A. D. Strosberg and P. O. Couraud. 1993. Nitric oxide and endothelin secretion by brain microvessel endothelial cells: regulation by cyclic nucleotides. *J. Cell. Physiol.* 155:104–111.

Franke, W. W., M. D. Goldschmidt, R. Zimbelmann, H. M. Mueller, D. L. Schiller, and P. Cowin. 1989. Molecular cloning and amino acid sequence of human plakoglobin, the common junctional plaque protein. *Proc. Natl. Acad. Sci. USA.* 86:4027–4031.

Frixen, U. H., J. Behrens, M. Sachs, G. Eberle, B. Voss, A. Warda, D. Lochner, W. Birchmeier. 1991. E-cadherin-mediated cell-cell adhesion prevents invasiveness of human carcinoma cell. *J. Cell Biol.* 113:173–185.

Gumbiner, B., and K. Simons. 1986. A functional assay for proteins involved in establishing an epithelial occluding barrier: identification of a uvomorulin-like polypeptide. *J. Cell Biol.* 102:457–468.

Gumbiner, B., B. Stevenson, and A. Grimaldi. 1988. The role of the cell adhesion molecule uvomorulin in the formation and maintenance of the epithelial junctional complex. *J. Cell Biol.* 107:1575–1587.

Hatzfield, M., G. I. Kristjansson, U. Plessmann, and K. Weber. 1994. Band 6 protein, a major constituent of desmosomes from stratified epithelia, is a novel member of the armadillo gene family. *J. Cell Sci.* 107:2259–2270.

Hedrick, L., K. R. Cho, and B. Vogelstein. 1993. Cell adhesion molecules as tumour suppressors. *Trends Cell Biol.* 3:36–39.

Herrenknecht, K., M. Ozawa, C. Eckerskorn, F. Lottspeich, M. Lente, and R. Kemler. 1991. The uvomorulin-anchorage protein alpha catenin is a vinculin homologue. *Proc. Nat. Acad. Sci. USA.* 88:9156–9160.

Hirano, S., A. Nose, K. Hatta, A. Kawakami, and M. Takeichi. 1987. Calcium-dependent cell-cell adhesion molecules (cadherins): subclass specificities and possible involvement of actin bundles. *J. Cell Biol.* 105:–2501–2510.

Hirano, S., N. Kimoto, Y. Shimoyama, S, Hirohashi; and M. Takeichi. 1992. Identification of neural α-catenin as a key regulator of cadherin function and multicellular organization. *Cell* 70:293–301.

Kanner, S. B., A. B. Reynolds, R. R. Vines, and J. T. Parsons. 1990. Monoclonal antibodies to individual tyrosine-phosphorylated protein substrates of oncogene-encoded tyrosine kinases. *Proc. Natl. Acad. Sci. USA.* 87:3328–3332.

Kanner, S. B., A. B. Reynolds, and J. T. Parsons. 1991. Tyrosine phosphorylation of a 120-kilodalton pp60$^{src}$ substrate upon epidermal growth factor and platelet-derived growth factor receptor stimulation and in polyomavirus middle-T-antigen-transformed cells. *Mol. Cell Biol.* 11:713–720.

Kikuchi, A., K. Kaibuchi, Y. Hori, H. Nonaka, T. Sakoda, M. Kawamura, T. Mizuno, and Takai, Y. 1992. Molecular cloning of the human cDNA for a stimulatory GDP/GTP exchange protein for c-Ki-ras p21 and smg p21. *Oncogene.* 7:289–293.

Kintner, C. 1992. Regulation of embryonic cell adhesion by the cadherin cytoplasmic domain. *Cell.* 69:225–236.

Kinzler, K. W., M. C. Nilbert, L. Su, B. Vogelstein, T. M. Bryant, D. B. Levy, K. Smith, A. C. Preisinger, P. Hedge, D. McKechnie, R. Finnear, A. Markham, J. Groeffen, M. S. Boguski, S. F. Altschul, A. Horii, H. Ando, Y. Miyoshi, Y. Miki, I. Nishisho, and Y. Nakamura. 1991. Identification of FAP Locus genes from chromosome 5q21. *Science.* 253:661–665.

Knudsen, K. A., and M. J. Wheelock. 1992. Plakoglobin, or an 83-kD homologue distinct from β-catenin, interacts with E-cadherin and N-cadherin. *J. Cell Biol.* 1992. 118:671–679.

Laemmli, U. K. 1970. Cleavage of structural proteins during the assembly of the head of bacteriophage T4. *Nature (Lond.).* 227:680–685.

Linder, M. E., and J. G. Burr. 1988. Nonmyristoylated p60$^{v-src}$ fails to phosphorylate proteins of 115–120 kDa in chicken embryo fibroblasts. *Proc. Natl. Acad. Sci. USA.* 85:2608–2612.

Matsuzaki, F., Mege, R.-M., S. H. Jaffe, D. R. Friedlander, W. J. Gallin, J. I. Goldberg, B. A. Cunningham, and G. M. Edelman, 1990. cDNAs of cell adhesion molecules of different specificity induce changes in cell shape and border information in cultured S180 cells. *J. Cell Biol.* 110:1239–1252.

McCrea, P. D., and B. M. Gumbiner. 1991. Purification of a 92-kDa cytoplasmic protein tightly associated with the cell-cell adhesion molecule E-cadherin (uvomorulin). Characterization and extractability of the protein complex from the cell cytostructure. *J. Biol. Chem.* 266:4514–4520.

McCrea, P. D., C. W. Turck, and B. Gumbiner. 1991. A homolog of the armadillo protein in Drosophila (plakoglobin) associated with E-cadherin. *Science.* 254:1359–1361.

Musil, L. S., Cunningham, B. A., Edelman, G. M., and D. Goodenough. 1990. Differential phosphorylation of the gap junction protein connexin43 in junctional communication-competent and -deficient cell lines. *J. Cell Biol.* 111:2077–2088.

Nagafuchi, A. and M. Takeichi. 1988. Cell binding junction of E-cadherin is regulated by the cytoplasmic domain. *EMBO (Eur. Mol. Biol. Organ.) J.* 7:3679–3684.

Nagafuchi, A., M. Takeichi, and S. Tsukita. 1991. The 102 kDa cadherin-associated protein: similarity to vinculin and posttranscriptional regulation of expression. *Cell.* 65:849–857.

Nelson W. J. 1992. Regulation of cell surface polarity from bacteria to mammals. *Science.* 258:948–955.

Ozawa, M., H. Baribault, and R. Kemler. 1989. The cytoplasmic domain of the cell adhesion molecule uvomorulin associates with three independent proteins structurally related in different species. *EMBO (Eur. Mol. Biol. Organ.) J.* 8:1711–1717.

Ozawa, M., M. Ringwald, and R. Kemler. 1990. Uvomorulin-catenin complex formation is regulated by a specific domain in the cytoplasmic region of the cell adhesion molecule. *Proc. Nat. Acad. Sci. USA* 87:4246–4250.

Peifer, M., and E. Wieschaus. 1990. The segment polarity gene armadillo encodes a functionally modular protein that is the Drosophila homolog of human plakoglobin. *Cell.* 63:1167–1176.

Peifer, M., P. D. McCrea, K. J. Green, E. Wieschaus, and B. M. Gumbiner. 1992. The vertebrate adhesive junction proteins β-catenin and plakoglobin and the Drosophila segment polarity gene armadillo form a multigene family with similar properties. *J. Cell Biol.* 118:681–691.

Peifer, M., S. Berg, and A. B. Reynolds. 1994. A repeating amino acid motif shared by proteins with diverse cellular roles. *Cell.* 76:789–91.

Piepenhagen, P. A., and W. J. Nelson. 1993. Defining E-cadherin-associated protein complexes in epithelial cells: plakoglobin, beta- and gamma-catenin are distinct components. *J. Cell Sci.* 104:751–762.

Reynolds, A. B., D. J. Roesel, S. B. Kanner, and J. T. Parsons. 1989. Transformation-specific tyrosine phosphorylation of a novel cellular protein in chicken cells expressing oncogenic variants of the Avian cellular src Gene. *Mol. Cell Biol.* 9:629–638.

Reynolds, A. B., L. Herbert, J. L. Cleveland, S. T. Berg, and J. R. Gaut. 1992. p120, a novel substrate of protein tyrosine kinase receptors and of p60$^{v-src}$, is related to cadherin-binding factors beta-catenin, plakoglobin and armadillo. *Oncogene.* 7:2439–2445.

Riggleman, B., E. Wieschaus, and P. Schedl. 1989. Molecular analysis of the armadillo locus: uniformly distributed transcripts and a protein with novel internal repeats are associated with a Drosophila segment polarity gene. *Genes Dev.* 3:96–113.

Rubin, L. L., D. E. Hall, S. Porter, K. Barbu, C. Cannon, H. C. Horner, M. Jantapour, C. W. Liaw, K. Manning, J. Morales, L. I. Tanner, K. J. Tomaselli, and F. Bard. 1991. A cell culture model of the blood-brain barrier. *J. Cell Biol.* 115:1725–1735.

Rubin, L. L. 1992. Endothelial cells: adhesion and tight junctions. *Curr. Opin. Cell Biol.* 4:830–833.

Rubinfeld, B., B. Souza, I. Albert, O. Muller, S. H. Chamberlain, R. H. Masiarz, S. Munemitsu, and P. Polakis. 1993. Association of the APC gene product with β-catenin. *Science.* 262:1731–1734.

Shimoyama, Y., S. Hirohashi, S. Hirano, M. Noguchi, Y. Shimosato, M. Takeichi and O. Abe. 1989. Cadherin cell-adhesion molecules in human epithelial tissues and carcinomas. *Cancer Res.* 49:2128–2133.

Shimoyama, Y., A. Nagfuchi, S. Fujita, M. Gotoh, M. Takeichi, S. Tsukita, and S. Hiroshashi. 1992. Cadherin dysfunction in a human cancer cell line: possible involvement of loss of α-catenin expression in reduced cell-cell adhesiveness. *Cancer Res.* 52:1–5.

Staddon, J. M., K. Herrenknecht, C. Smales, and L. L. Rubin. Evidence that tyrosine phosphorylation may increase tight junction permeability. *J. Cell Sci.* in press.

Su, L. K., B. Vogelstein, and K. W. Kinzler. 1993. Association of the APC tumor suppressor protein with catenins. *Science.* 262:1734–1737.

Takeichi, M. 1991. Cadherin cell adhesion receptors as morphology regulators. *Science.* 251:1451–1455.

Tsukita, S., K. Oishi, A. Akiyama, Y. Yamanishi, T. Yamamoto, and S. Tsukita. 1991. Specific protooncogenic tyrosine kinases of src family are enriched in cell-to-cell adherens junctions where the level of tyrosine phosphorylation is elevated. *J. Cell Biol.* 113:867–879.

Tsukita, S., M. Itoh, A. Nagatuchi, and S. Yonemura. 1993. Submembranous junctional plaque proteins include potential tumour suppressor molecules. *J. Cell Biol.* 123:1049–1053.

Vleminckx, K., L. Vakaet, M. Jr. Mareel, W. Fries, and F. Van Roy. 1991. Genetic manipulation of E-cadherin expression by epithelial tumor cells reveals an invasion suppressor role. *Cell.* 66:107–119.

Tano, R., M. L. Oakes, M. Yamaghishi, J. A. Dodd, and M. Nomura. 1992. Cloning and characterization of SRP1, a suppressor of temperature-sensitive RNA polymerase I mutations, in *Saccharomyces cerevisiae. Mol. Cell. Biol.* 12:5640–5651.

Yano, R., M. L. Oakes, M. M. Taub, and M. Nomura. 1994. Yeast Srp1p has homology to armadillo/plakoglobin/β-catenin and participates in apparently multiple nuclear functions including the maintenance of the nucleolar structure. *Proc. Natl. Acad. Sci. USA.* 91:6880–6884.

What is claimed is:

1. A substantially pure protein p100 having a molecular weight of about 100 kDa as determined by sodium dodecyl sulfate polyacrylamide gel electrophoresis (SDS-PAGE) under reducing conditions, wherein said p100 comprises one or more of the following amino acid sequences:

(i) NISFGRDQDNK (SEQ ID NO:1), (ii) HAIPNLV (SEQ ID NO:2), (iii) XVLINK (SEQ ID NO:3), (iv) XPIEDPANDTVDFPX (SEQ ID NO:4), and (v) XPSGALRNLAVDARX (SEQ ID NO:5), wherein the letters used are based on the standard single letter amino acid code, and wherein "X" designates any amino acid;

wherein said protein is associated in vivo with the catenin-cadherin complex of epithelial or endothelial cells;

wherein said protein has cross-reactivity with an antibody to p120; and wherein said protein is not recognized by antibody rr1;

with the proviso that said protein is not p120.

2. The protein of claim 1, wherein said protein is human p100.

* * * * *

```
                        SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 11 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 1:

Asn Ile Ser Phe Gly Arg Asp Gln Asp Asn Lys
1               5                   10

(2) INFORMATION FOR SEQ ID NO: 2:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 2:

His Ala Ile Pro Asn Leu Val
1               5

(2) INFORMATION FOR SEQ ID NO: 3:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 3:

Xaa Val Leu Ile Asn Lys
1               5

(2) INFORMATION FOR SEQ ID NO: 4:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 4:

Xaa Pro Ile Glu Asp Pro Ala Asn Asp Thr Val Asp Phe Pro Xaa
1               5                   10                  15
```

(2) INFORMATION FOR SEQ ID NO: 5:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 5:

Xaa Pro Ser Gly Ala Leu Arg Asn Leu Ala Val Asp Ala Arg Xaa
1               5                   10                  15

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 6:

His Ala Arg Pro Asn Leu Val
1               5

(2) INFORMATION FOR SEQ ID NO: 7:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 7:

Leu Val Leu Ile Asn Lys
1               5

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 8:

Lys Pro Thr Glu Asp Pro Ala Asn Asp Thr Val Asp Phe Pro Xaa
1               5                   10                  15

(2) INFORMATION FOR SEQ ID NO: 9:

(i) SEQUENCE CHARACTERISTICS:
        (A) LENGTH: 15 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 9:

Ala Ala Ser Gly Ala Leu Arg Asn Leu Ala Val Asp Ala Arg Lys
1               5                   10                  15